United States Patent [19]
Burton

[11] Patent Number: 5,282,863
[45] Date of Patent: Feb. 1, 1994

[54] FLEXIBLE STABILIZATION SYSTEM FOR A VERTEBRAL COLUMN

[75] Inventor: Charles V. Burton, 148 W. Lake St., Excelsior, Minn. 55331

[73] Assignee: Charles V. Burton, Excelsior, Minn.

[21] Appl. No.: 921,351

[22] Filed: Jul. 24, 1992

Related U.S. Application Data

[63] Continuation of Ser. No. 571,037, Aug. 21, 1990, abandoned, which is a continuation of Ser. No. 442,478, Nov. 22, 1989, abandoned, which is a continuation of Ser. No. 154,000, Feb. 9, 1988, abandoned, which is a continuation-in-part of Ser. No. 742,923, Jun. 10, 1985, Pat. No. 4,743,260.

[51] Int. Cl.$^5$ .......................... A61F 2/44; A61F 5/04
[52] U.S. Cl. ........................................ 623/17; 606/61
[58] Field of Search ............... 623/17, 16, 18; 606/60, 606/61, 72, 73, 74

[56] References Cited

U.S. PATENT DOCUMENTS

| | | | |
|---|---|---|---|
| 3,579,831 | 5/1971 | Stevens et al. | 433/174 |
| 3,648,691 | 3/1972 | Lumb et al. | |
| 3,855,638 | 12/1974 | Pilliar | 623/16 |
| 3,988,783 | 11/1976 | Treace | 128/92 B |
| 4,177,524 | 12/1979 | Grell et al. | 623/16 |
| 4,244,689 | 1/1981 | Ashman | 433/175 |
| 4,351,069 | 9/1982 | Ballintyn | 128/92 YF X |
| 4,403,607 | 9/1983 | Woo et al. | 128/92 YP |
| 4,506,681 | 3/1985 | Mundell | 128/92 YP X |
| 4,611,581 | 9/1986 | Steffee | |
| 4,722,870 | 2/1988 | White | 623/16 |
| 4,722,870 | 2/1988 | White | 623/16 X |

FOREIGN PATENT DOCUMENTS 3132520 6/1982 Fed. Rep. of Germany .
624625 9/1978 U.S.S.R. .................. 128/69

OTHER PUBLICATIONS

Miner. Sci. Engng, vol. 5, No. 2, Apr. 1973, pp. 151-162, Carbonate Minerals as Precursors of New Ceramic, Metal, and Polymer Materials for Biomedical Applications.
The Journal of Bone and Joint Surgery, vol. 56B, No. 2, May 1974, pp. 218-224, Anterior Approach to Scoliosis.
Campbell's Operative Orthopaedics, pp. 2054-2055.
Clinical Orthopaedics and Related Research, No. 180, Nov. 1983, pp. 133-153, Zielke Instrumentation (VDS) for the Correction of Spinal Curvature.
Macey; Mayo Clinic Staff Meeting, pp. 613-618, Sep. 1936.

*Primary Examiner*—David Isabella
*Attorney, Agent, or Firm*—Merchant, Gould, Smith, Edell, Welter & Schmidt

[57] ABSTRACT

A device and method for a flexible stabilization system for a vertebral column is disclosed. The device includes a strong, non-metallic stabilization element or elements for providing flexibility. The stabilization elements are secured to the vertebrae and wherein, when secured, the stabilization element or elements stabilize the vertical column while still allowing for flexibility. In a preferred embodiment the stabilization elements are anchored to the vertebrae by a bone screw having an upper shank portion and a lower threaded portion having segmented area. Still further, the bone screw and stabilization elements may be porous and produced from material made by the replamineform process.

8 Claims, 3 Drawing Sheets

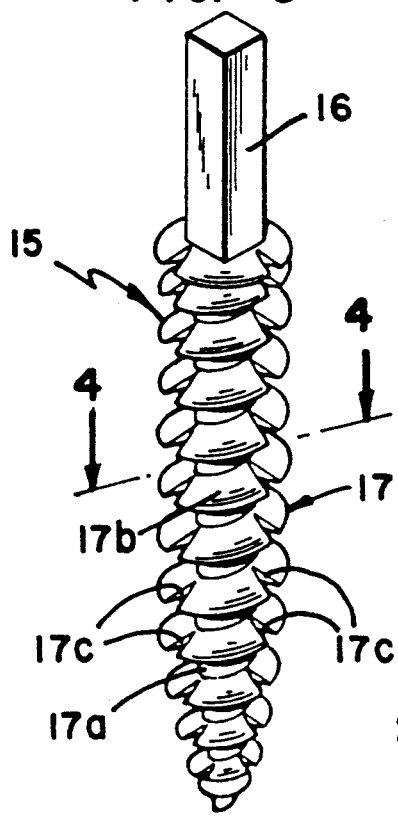
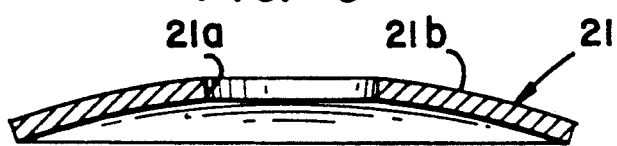
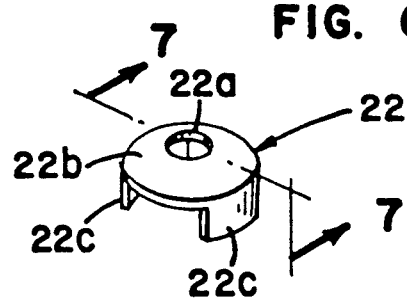
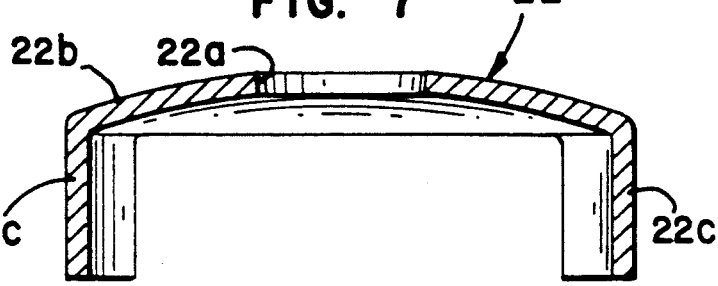
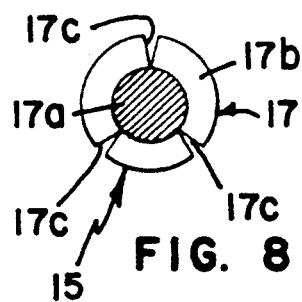
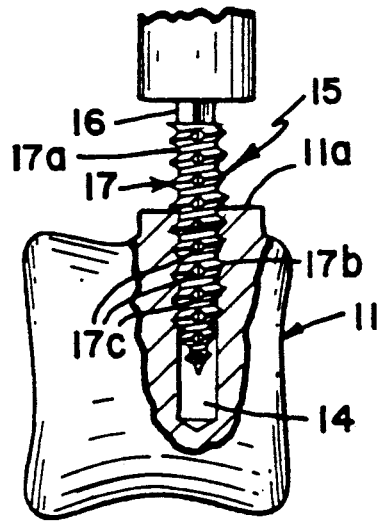
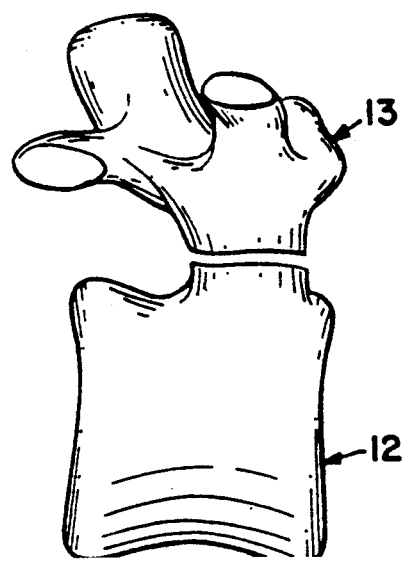

FLEXIBLE STABILIZATION SYSTEM FOR A VERTEBRAL COLUMN

This is a continuation of application Ser. No. 07/571,037, filed Aug. 21, 1990, now abandoned, which is a continuation of Ser. No. 07/442,478, filed Nov. 22, 1989, now abandoned, which is a continuation of Ser. No. 07/154,000, filed Feb. 8, 1988, now abandoned, which is a continuation-in-part of Ser. No. 06/742,923, filed Jun. 10, 1985, now U.S. Pat. No. 4,743,260.

BACKGROUND OF THE INVENTION

1. Field of the Invention

This invention relates generally to a non-metallic device and method for the stabilization of at least a portion of a vertebral column and more particularly to a device and method for spinal stabilization and also which incorporates a microporous material.

2. Description of the Prior Art

Fusion of vertebral columns by instrumentation devices and/or bone material is common and a long practiced surgical technique. Fusion is the permanent internal fixation of part or all of the intervertebral joints, an intervertebral joint being composed of two adjacent vertebrae and their posterior bony elements connected by an intervertebral disc, ligaments, and two facet joint capsules. However, the concept of fusion carries significant and previously unappreciated patient disability. By fusing vertebrae the remaining segments are subject to inordinately high stress and degeneration. In the typical L4-S1 fusion the L3-4 level typically undergoes dramatic degeneration of the disc and zygoapophyseal joints leading to the production of a clinical entity called the "transitional syndrome" often leading to "mechanical-type" pain or actual spinal nerve compression. The stress patterns produced by fusion often produce clinical problems relating to the sacro-iliac and hip joints.

When spine fusions involve mechanical instrumentation, significant forces are directly aimed at the supportive sites whether they be bone screws, hooks, etc. This phenomenon usually produces loosening of the points of attachment for the implanted hardware and a resulting loss of support by this instrumentation. Because of this, fusions involving instrumentation are often carried out in conjunction with bone fusions so as the instrumentation loosens and fails, support can be maintained by growth of the bony counterpart. These combined procedures involve extensive surgery, substantial blood loss and high cost. Following such a procedure, patients are usually disabled for long periods of time.

Therefore, the treating of spinal instability by fusion is not optimal. It immobilizes adjacent segments, eliminating their previous natural ability to move relative to each other. Further, when fusion has taken place with the addition of internal fixation, often the internal fixation parts are of a metallic nature. In modern medical practice the presence of dense metallic devices is a significant liability due to the scattering artifacts generated if imaging is attempted. Since the spinal diagnostic procedure of choice is now imaging, the presence of significant metallic objects represents a serious diagnostic limitation.

In 1973 scientists at the Materials Research Laboratory at Penn State University observed that is some reef building corals their microstructure was characterized by 1) a high degree of uniformity in pore diameter, 2) a pore interconnection diameter similar in size to that of the pore itself, 3) a solid-to-volume ratio or approximately one, and 4) exceptionally high permeability in which each and every pore was interconnected to all other pores. It was recognized that it would be virtually impossible to achieve these structural characteristics by artificial means. Early experiments designed to impregnate the coral with various substances, dissolve the calcium carbonate coral skeleton and then make positive casts with other materials including metal alloys were successful and the term "the replamineform process" was coined.

In addition to replamineform casting it became evident that the structural characteristics of coral itself could possibly serve as the means for bone ingrowth after cleansing of organic materials and chemical conversion from biogenic carbonate to hydroxyapetite.

Subsequent medical studies using coral with a microdiameter (200–250 microns) similar to that of the normal human bone Haversian canals (200–400 microns) were conducted by a number of physicians in the United States. Drs. Vert Mooney and David Selby in Dallas, Tex. performed 40 cases of bilateral spinal bone fusion in which one side was coral provided by Interpore International of Irvine, Calif., and the other side autogenous bone. These studies did not demonstrate significant ingrowth of osteoblasts into the coral and these observations led to the conclusion that coral showed little value in this regard. Since this work most clinicians have almost exclusively used autogenous or donor derived homologous bone.

The present invention addresses the problems associated with the prior art devices and method for treating spinal instability and provides for stabilization, rather than fusion, that is, support with the allowance of some natural movement or flex, and accomplishes this with a minimal amount of metallic components and may allow for ingrowth by fibroblasts to occur.

SUMMARY OF THE INVENTION

The present invention is a device and method for stabilizing a portion of a vertebral column without fusion. In the preferred form the stabilization device of the present invention is substantially completely or completely made of non-metallic materials (e.g. plastic) which are biocompatible.

The vertebral column is composed of segments of adjacent vertebrae, with the first vertebra being adjacent the second vertebra. Each vertebra has a posterior vertebral element which, when removed, leaves first and second pedicles on each of the vertebra. The present device includes a strong nonmetallic anchor means for securing the stabilization means to at least one of the pedicles of the first and second vertebrae and means for cooperatively connecting the stabilization means to the anchor means. In a preferred embodiment, the device further includes a means for locking the stabilization means to the anchor means.

In a preferred embodiment, the anchor means includes an upper shank portion and a lower threaded portion having a screw thread. The lower portion is cooperatively connected to the shank portion. The screw thread has segmented areas, wherein a rotary force may be applied to the shank portion whereby the threaded portion is driven into and secured into the pedicles. The screw thread may have segmented areas, wherein after a period of time the vertebra's bony regrowth encompasses the segmented areas to further secure the threaded portion to the pedicles.

In a preferred embodiment the stabilization means includes a first stabilization element having first and second openings and a second stabilization element having first and second openings. The anchor means comprises four support members such that one of the support members is secured to each of the pedicles, wherein each of the openings is adapted for being positioned around one of the support members. The stabilization elements may then be aligned along the four support members in either a generally parallel relationship or in an X shape. Further, a cross support member may be used to further connect the first stabilization element to second stabilization element.

In a preferred embodiment, the anchoring means and/or stabilization means may be made from a microporous material produced by a suitable process such as a replamineform process, wherein ingrowth by fibroblasts occur. Coral having a microdiameter of between 190–1200 microns and preferably between 190–230 microns in diameter is used and poritic corals may be used as a model for the replamineform process.

The present invention also comprises a surgical method for stabilizing a portion of a vertebral column without fusion. The method includes making an incision to expose the first and second vertebrae. Then, the posterior vertebral elements of each of the vertebrae to be stabilized are removed, leaving first and second pedicles of the first vertebra and first and second pedicles of the second vertebra. A bone screw is secured into at least one of the pedicles of the first and second pedicles of the first and second vertebrae. The bone screw has a threaded bottom portion and an upper shank portion, Then, the stabilization means is cooperatively connected between the bone screw of one of the first pedicles of the first vertebra to the bone screw of one of the first pedicles of the second vertebra. It is understood that screws are not essential, but are a preferred embodiment. Other suitable anchoring means may be used to anchor the stabilization means to pedicles, such as stapling. It is also understood that multiple segments may be stabilized.

BRIEF DESCRIPTION OF THE DRAWINGS

FIG. 3 is a perspective view of the bone screw of the present invention.

FIG. 4 is a cross-sectional view taken generally along the lines 4—4 of FIG. 3.

FIG. 5 is a cross-sectional view of one embodiment of the locking cap as shown in FIG. 1.

FIG. 6 is a perspective view of a second embodiment of a locking cap.

FIG. 7 is a cross-sectional view taken generally along the lines 7—7 of FIG. 6.

FIG. 8 is a partial cross-sectional view showing a bone screw being inserted into a vertebra according to the present invention.

FIG. 9 is a side-elevational view of a vertebra before the posterior vertebral elements are removed according to the present invention.

DETAILED DESCRIPTION OF A PREFERRED EMBODIMENT

Figure 1:
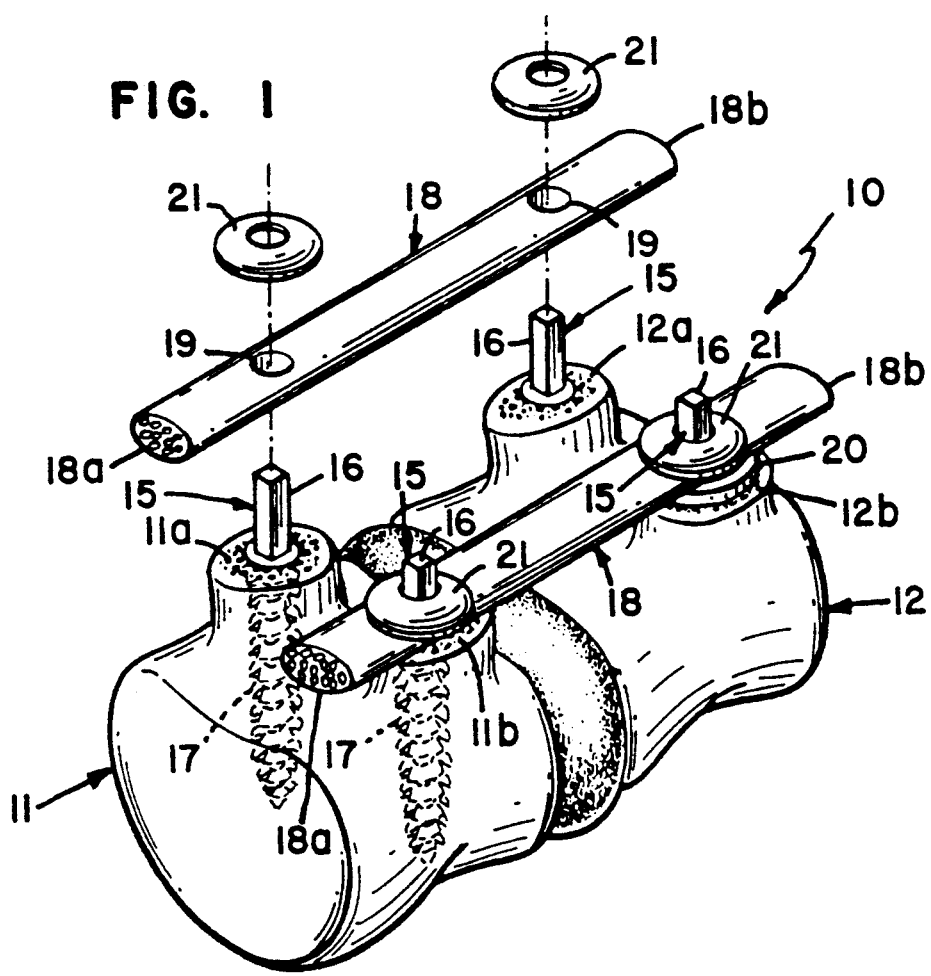
FIG. 1 is a perspective view showing one embodiment of the present invention in a partially exploded perspective view.

Referring to the figures, wherein like numerals represent like parts throughout the several views. there is generally illustrated at 10 a device for stabilizing at least a portion of a vertebral column. In FIG. 1, a first vertebra 11 and second vertebra 12 are shown. It should be understood that when first and second vertebrae are used in this application, it is only in reference to vertebrae that are adjacent, and not to any specific vertebrae along the vertebral column. Each vertebra has a posterior element, designated as 13 shown in FIG. 9. When the posterior element 13 is removed from the vertebra, a first and second vertebral pedicle is exposed in each vertebra. FIG. 1 shows the first vertebral pedicle 11a and second vertebral pedicle 11b of the first vertebra 11 and first vertebral pedicle 12a and second vertebral pedicle 12b of the second vertebra 12. If screws are used as anchoring devices, each of the pedicles (11a, 11b, 12a or 12d) that are to be utilized have a hole 14 drilled into the pedicle.

A bone screw, generally designated as 15, has an upper shank portion 16, that in a preferred embodiment, has a square cross section to allow for efficient insertion and removal. A lower threaded portion 17 is cooperatively connected to the upper shank portion 16. The threaded portion 17 has an inner shaft 17a and a threaded member 17b. The threaded member 17b is a continuous helical member having segmented areas 17c. The threaded member 17 provides a wide flange to give a deep bite when secured in the vertebra. While the segmented areas 17c are shown in FIG. 4 as being pie-shaped, and having three per one complete circumference, it is understood that any suitable shape or number of segmented areas may be utilized. The inner shaft 17a and threaded member 17b have a generally consistent diameter throughout, except for a taper towards a point at their bottom end. Preferably, the diameter of the hole 14 is slightly smaller than the diameter of the inner shaft 17a.

A stabilization element 18, having a first end 18a and a second end 18b has two openings 19 adapted to being placed over the upper shank 16 of the bone screw 15. A spacer 20 may also be used if the height of the pedicle is not sufficient. The spacer 20 can be inserted between the pedicle and stabilization element 18 to avoid compression of exiting spinal nerves. In one embodiment, the element 18 is a flat strip. However, it is understood that other suitable shapes such as an hour glass shape or dumbbell shape may be used.

A locking cap 21, having an opening 21a has a generally downwardly depending circumferential member 21b that locks the rod 18 in place. A second embodiment of a locking cap is shown in FIGS. 6 and 7. The locking cap 22 is similar to the locking cap 21 in that it has an opening 22a and a generally downwardly depending circumferential member 22b, similar to locking cap 21. However, in addition, there are two skirt members 22c. As will be more fully discussed hereinafter, the skirt members 22c limit parallelogram movement between the two stabilization elements 18 when they are in position.

The material that the stabilization elements 18 and screws 15 are made of must provide sufficient strength. be bio-compatible, and preferably non-metallic. Some non-reinforced bio-compatible plastic polymers indicate a tendency to crack, fissure or shear with repeated flex or stress. A preferred material is a two-phase bio-compatible plastic so as to provide adequate strength. Internal reinforcement with dissimilar polymers or filaments provide increased strength over that of a single phase plastic, but as the internal diameter of the stabilization element 18 decreases, practical fabrications become a problem. Therefore, it is preferred that internal fibers be used for reinforcement. It is desired that the material used have sufficient strength and flexibility, as well as being biocompatible.

It is known that many fibers have been tested in polymers and many lightweight and remarkably strong materials have resulted. A most innovative reinforced two-phase material to date have been created for aeronautical use. Although many of these systems are attractive for their physical qualities, they are also marginal or clearly unacceptable from the standpoint of being biocompatible. It has been found that carbon fiber reinforced plastic yields adequate strength for constructing the stabilization elements 18. However, it is sometimes preferable that the screws be made of a still stronger material so as to prevent the screws from being sheared off by the stress of the system. One such material that has been found adequate for the screws 15 is a magnamite graphite fiber or carbon reinforced plastic. The materials used for the stabilization elements 18 and screws 15 are not limited to the above noted plastics, and may also include other suitable solid materials that have the above-noted properties. Also, porous material forms in which the porosity is controlled by the replamineform process may be utilized. Polymers such as silicone, polyethylene, nylon, vinyl, methylmethacyrate, dacrons or teflon may be suitable.

Applicant has made a study of small coral specimens and a study of these samples has confirmed the original observations of the Penn State researchers. By matching the physical pore size characteristics of applicant's samples with those reported in the failed medical fusion studies, two conclusions can be drawn. The first is that if coral with larger pore sizes were used (400-500 microns), it might very well be more successful for bone fusion osteoblasts ingrowth. Secondly, the previous medical research on coral which was considered a failure actually indicated that there was ingrowth by fibroblasts (rather than osteoblasts). However, such fibroblasts ingrowth is well suited for the flexible system of the present invention. The ingrowth of fibroblasts will further anchor and fix the device 10, but will still allow the device 10 to retain its flexible characteristics.

Further, Applicant has identified poritic coral having 190-230 micron diameter as preferred for the present flexible system rather than other corals, such as goniopera with 230-600 micron size. It is poritic coral which would serve as the replamineform model for making the screws 15 and stabilization elements 18 of the present invention. However, it has been found that pore sizes of from 190-1200 microns are suitable for the present invention.

Figure 2:
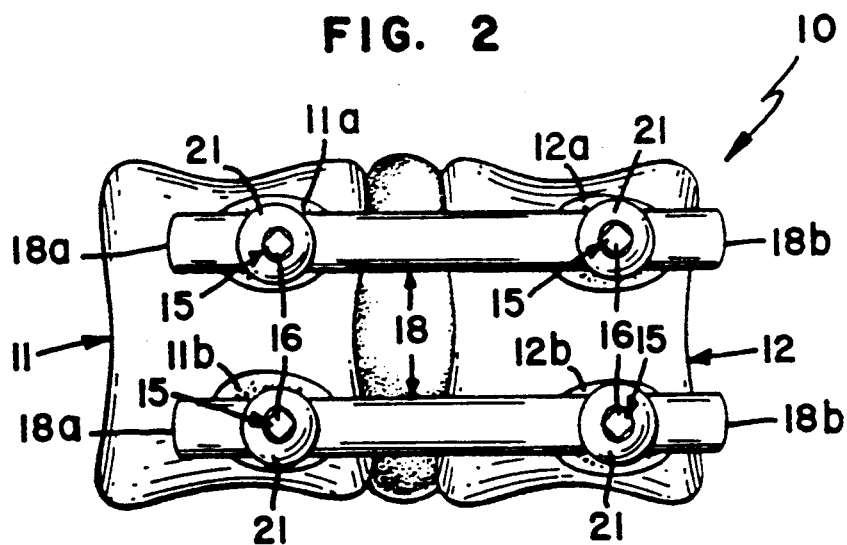
FIG. 2 is a top-plan view of the present invention shown in FIG. 1.

In use, only a limited surgical exposure is necessary to perform the operation necessary to incorporate the present invention. Following the removal of the posterior vertebral elements 13, the exposed pedicles serve as the anchoring media for the bone screws 15. The pedicles are drilled by appropriate means to create the hole 14. A driving mechanism is placed over the upper shank 16 and the lower portion 17 is screwed completely into the vertebra. The threaded member 17b serves to stabilize the bone screw 15 and the segmented areas 17c are designed to allow bone growth to further stabilize the screw 15 in place. If only two vertebrae are to be stabilized, it is only necessary for bone screws 15 to be secured into the pedicles 11a, 11b, 12a and 12b. However, if multiple vertebrae are to be stabilized, the corresponding pedicles on the third or subsequent vertebrae would also have to be provided with a bone screw 15. The stabilization elements 18 are tapped at the appropriate position and holes 19 are made either by drilling or by a heated rod at the site of the tap. While FIGS. 1 and 2 show that stabilization elements 18 have been placed for a one-level stabilization, the present invention is compatible with stabilizing multiple levels as well as single levels. Further, only one stabilization element 18 may be necessary for some patients. Once the screws 15 are in place, a separator instrument, not shown, may be used to distract the vertebrae, if this desired, and this separation is maintained by the placement of the stabilization elements 18 over the shank 16 of the bone screw 15. As previously mentioned, if the height of the pedicle is not sufficient, a spacer 20 may be inserted on top of the pedicle. The spacer 20 may be constructed from a softer plastic such as polyurethane or silicone. The procedure is then completed by the application of a locking cap, either 21 or 22, at each of the upper shanks 16 and the removal of any excess shank material above the top of the locking cap 21 or 22.

While the device 10 is illustrated in FIGS. 1 and 2 as having a stabilized means having two generally parallel stabilization elements 18, it is understood that the stabilization means may be other suitable forms such as a single stabilization element 18, or two stabilization elements 18 that cross to form an X shape, or two stabilization elements 18 generally parallel having across support member to form an H shape.

The present invention allows for flexibility and because of the flexibility of the system, less disruptive force is applied to the screw 15, or other anchor means, following the application of the system itself.

The flexibility of the device 10 has as its lower limit no flexibility. No flexibility would have the same result as fusion and the device 10 provides for at least some flexibility more than fusion. In the preferred embodiment, the flexibility of the device 10 would stabilize with a degree that substantially equals a normal back. Too much flexibility would render the back non-functional and not stabilize the back. Any stabilization more than that present in the back of the patient before the procedure would be beneficial. Numerically, the general upper limit of flexibility for the device 10 is shown in the following table for the stabilization means:

| Stabilization Means Length | Inch-Pounds for Standard Deflection of ¼ Inch |
| --- | --- |
| 1" | 45 ip. |
| 2" | 32 ip. |
| 3" | 23 ip. |

The device 10 is stiff enough to stabilize the vertebral column but flexible enough to permit at least limited normal movement of the vertebral column. The flexibility allows forces on the stabilization elements and anchors to be dissipated throughout, thereby reducing force concentrations.

If locking cap 21 is used, parallelogram movement between the two stabilization elements 18 is possible. That is, there is a possibility of some relative sideways movement of the first vertebra 11 to the second vertebra 12. If locking cap 22 is used, the locking cap 22 will limit the parallelogram movement. This is because the rod 18 is positioned inside of the skirt member 22c such that parallelogram rotation is limited.

In addition to anchoring the stabilization element 18 by means of screws 15, it is also envisioned that other suitable methods of anchoring may be used. One such example would be to staple the stabilization element 18 to the pedicles. Another embodiment would include ribbed tabs molded to the stabilization element 18 as an integral part thereof and would be positioned approximately the same place where the bone screws 15 would be inserted in the previously discussed embodiment. The holes would then be drilled into the pedicles at the appropriate distances and the ribbed tabs could be inserted into the holes and glued in place. The ribbed tabs could be placed at varying distances along the stabilization element in various models and the appropriate length model simply chosen depending upon the spacing between the vertebrae of the patient.

Figure 10:
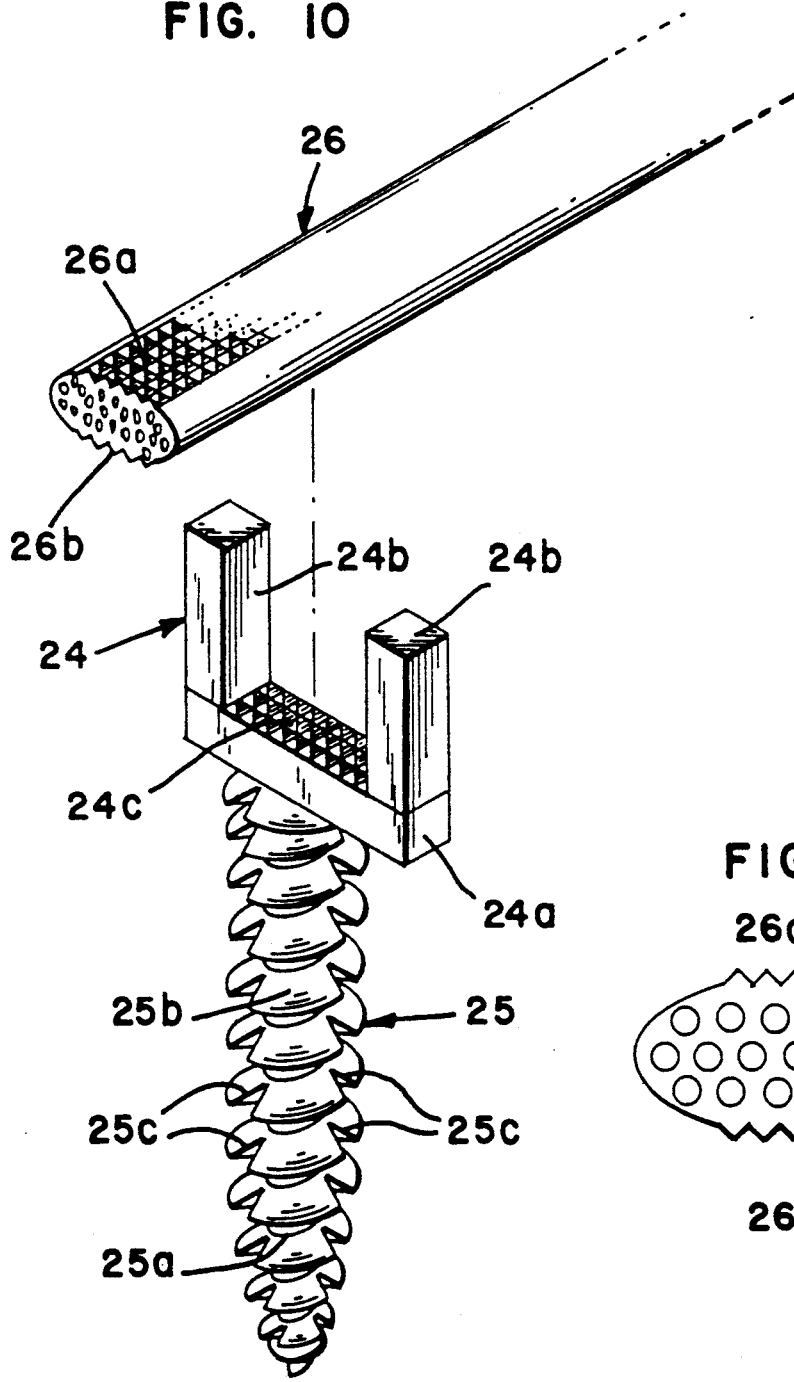
FIG. 10 is perspective view of a second embodiment of a bone screw.
Figure 11:
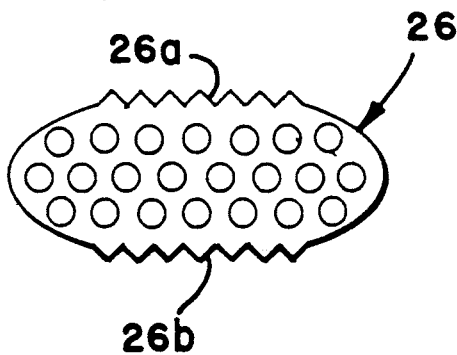
FIG. 11 is a perspective view of a second embodiment of a stabilization element.

FIGS. 10 and 11 show another embodiment of the present invention wherein it would not be necessary to have an opening in the stabilization rod. The second embodiment of the bone screw 23 has an upper portion 24 and a lower threaded portion 25. The lower threaded portion 25 is similar to the lower threaded section 17 in that the lower portion 25 has a shaft 25a about which is threaded members 25b having segmented areas 25c. The upper portion 24 has a base 24a and two upright members 24b cooperatively connected thereto. The top surface of the base 24a has a corrugated area 24c.

The second embodiment of the stabilization element, designated as 26 has a corrugated upper surface 26a and a corrugated bottom surface 26b. The corrugated surfaces 26a, 26b and 24c could also be described as having a vertical toothed surface. The toothed surface 26b meshes with the toothed surface 24c, thereby preventing relative movement between the stabilization element 26 and the bone screw 23. With such a vertical tooth configuration, it is not necessary to create an opening in the stabilization element 26. The uprights 24b are spaced to have a distance between them the approximate width of the stabilization element 26. Therefore the upright members 24b also assist in limiting relative movement of the stabilization element 26 to the bone screw 23.

The present invention represents an important advance in spinal stabilization technology. The system provides for limited surgical exposure, limited operating time, lower cost and is a simpler operation than fusion. Further, the method is conducive to revision if the status of the patient changes. By allowing some motion in the system, stress on the anchoring device as well as adjacent vertebrae have been reduced. The unique nature of this stabilization system is such that its applicability will not only involve fusion candidates, but will also involve extension to impaired individuals not presently considered to be treatable.

Other modifications of the invention will be apparent to those skilled in the art in light of the foregoing description. This description is intended to provide specific examples of individual embodiments which clearly disclose the present invention. Accordingly, the invention is not limited to these embodiments or the use of elements having specific configurations and shapes as presented herein. All alternative modifications and variations of the present invention which follows in the spirit and broad scope of the appended claims are included.

What is claimed is:

1. A spinal implant device for stabilizing a portion of a vertebral column without fusion, the vertebral column having first and second vertebrae which have posterior vertebral elements removed, the first vertebra being adjacent the second vertebra, each vertebra having a posterior vertebral element which when removed leaves first and second pedicles on each of the vertebra, the pedicles having a top surface, said device comprising:
   (a) a strong, plastic, biocompatible stabilization means having first and second ends to stabilize the vertebral column but flexible enough to provide at least limited normal movement of the vertebral column; and
   (b) anchoring means for securing said stabilization means to the pedicles, said anchoring means having means for fastening said first end of said stabilization means to said one of the top surface of the pedicles of the first posterior element and said second end of said stabilization means to said one of the top surface of the pedicles of the second posterior element, said anchoring means adapted to be driven into and secured into the top surfaces of the pedicles, wherein when secured said stabilization means stabilizes the vertebral column while still allowing for flexibility to that forces on the stabilization means are dissipated throughout, thereby reducing force concentration.

2. The device of claim 1, further comprising means for locking said stabilization means to said anchor means.

3. The device of claim 1, wherein said anchor means comprises:
   (a) an upper shank portion; and
   (b) a lower threaded portion having a screw thread, said lower portion cooperatively connected to said shank portion, said screw thread having segmented areas, wherein a rotary force may be applied to said shank portion whereby said threaded portion is driven into and secured into the pedicles.

4. The device of claim 3, wherein said anchoring means is of a bio-compatible plastic.

5. The device of claim 1, wherein said stabilization means comprises a first rod having a first and second openings, and a second rod having first and second openings, and wherein said anchor means comprises four support members such that one of said support members is secured to each of the pedicles, wherein each of said openings is adapted for being positioned around one of said support members.

6. The device of claim 1, further comprising a spacer positioned between said stabilization means and one of the posterior elements.

7. The device of claim 1, wherein said anchor means and stabilization means are porous and of suitable size for fibroblast ingrowth.

8. The device of claim 7, wherein said anchor means and stabilization means having a porosity with pore diameters from 190 to 230 microns.

* * * * *